United States Patent [19]

Sasaki et al.

[11] Patent Number: 4,774,352
[45] Date of Patent: Sep. 27, 1988

[54] PROCESS FOR AMMOXIDATION

[75] Inventors: Yutaka Sasaki; Yutaka Kiyomiya; Toshio Nakamura, all of Kanagawa, Japan

[73] Assignee: Nitto Chemical Industry Co., Ltd., Japan

[21] Appl. No.: 808,684

[22] Filed: Dec. 17, 1985

Related U.S. Application Data

[63] Continuation of Ser. No. 426,536, Sep. 29, 1982, abandoned.

[30] Foreign Application Priority Data

Oct. 7, 1981 [JP] Japan .................. 56-159703
Feb. 16, 1982 [JP] Japan .................. 57-21993

[51] Int. Cl.[4] .................. C07C 120/00; C07C 120/14
[52] U.S. Cl. .................. 558/322; 423/376; 546/286; 558/319; 558/321; 558/327; 558/328
[58] Field of Search ............ 558/322, 329, 319, 321, 558/327, 328; 423/376

[56] References Cited

U.S. PATENT DOCUMENTS

| | | | |
|---|---|---|---|
| 3,164,626 | 1/1965 | Minekawa et al. | 260/465.3 |
| 3,164,627 | 1/1965 | Minekawa et al. | 260/465.3 |
| 3,164,628 | 1/1965 | Minekawa et al. | 260/465.3 |
| 3,290,354 | 12/1966 | Eden | 260/465.3 |
| 3,335,169 | 8/1967 | Eden | 260/465.3 |
| 3,392,187 | 7/1968 | Eden | 260/465.3 |
| 3,392,188 | 7/1968 | Eden | 260/465.3 |
| 3,392,189 | 7/1968 | Eden | 260/465.3 |
| 3,396,189 | 8/1968 | Eden | 260/465.3 |
| 3,412,135 | 11/1968 | Eden | 260/465.3 |
| 3,417,125 | 12/1968 | Eden | 260/465.3 |
| 3,417,128 | 12/1968 | Eden | 260/465.3 |
| 3,426,059 | 2/1969 | Eden | 260/465.3 |
| 3,426,060 | 2/1969 | Eden | 260/465.3 |
| 3,445,500 | 5/1969 | Eden | 260/465.3 |
| 3,641,102 | 2/1972 | Reulet et al. | 260/465.3 |
| 3,898,267 | 8/1975 | Caporali et al. | 260/465.3 |
| 3,928,409 | 12/1975 | Pignataro et al. | 260/465.3 |
| 4,316,855 | 2/1982 | Grasselli et al. | 260/465.3 |
| 4,339,394 | 7/1982 | Grasselli et al. | 260/465.3 |
| 4,409,122 | 10/1983 | Kleuskens | 260/465.3 |

*Primary Examiner*—Joseph P. Brust
*Attorney, Agent, or Firm*—Sughrue, Mion, Zinn, Macpeak, and Seas

[57] ABSTRACT

The activity of a tellurium-free metal oxide catalyst used for ammoxidation of organic compounds at a temperature of from 300° C. to 600° C. is improved in the presence of (a) elemental tellurium or a tellurium compound which is in contact with said catalyst or in the presence of (a) elemental tellurium or a tellurium compound and (b) a molybdenum compound which are in contact with said catalyst. This activity improvement process can be applied to both the fresh catalysts and the spent catalyst having a deteriorated activity. The above described component (a) is preferably composed of a tellurium containing solid to be used in a state of a dry physical mixture with said catalyst. The above described components (a) and (b) are preferably composed of a tellurium containing solid and a molybdenum containing solid respectively or a tellurium-molybdenum containing solid to be used in a state of a dry physical mixture with said catalyst.

The tellurium containing solid, the molybdenum containing solid or the tellurium-molybdenum containing solid may be at least a member selected from the following group:

(1) A solid wherein a tellurium component and/or a molybdenum component is supported or unsupported on an inert carrier, (2) A solid wherein a tellurium component and/or a molybdenum component is added to a metal oxide catalyst (fresh or spent) and/or said metal oxide catalyst is enriched with the tellurium component and/or the molybdenum component, and (3) A solid composed of a compound containing at least one element selected from the group consisting of an alkali metal, an alkaline earth metal, La, Ce, V, Nb, Cr, W, Mn, Fe, Co, Ni, Cu, Zn, Cd, B, Al, Ga, Ge, Sn, Pb, P, AS, Sb, Bi, S and Se in addition to tellurium, molybdenum or tellurium and molybdenum, or a mixture of these compounds, supported or unsupported on an inert carrier.

The present invention is advantageously applied to ammoxidation in a fluidized bed.

1 Claim, No Drawings

PROCESS FOR AMMOXIDATION

This is a continuation of application Ser. No. 426,536, filed 9/29/82, now abandoned.

FIELD OF THE INVENTION

The present invention relates to an improvement of a process for ammoxidation of organic compounds and, more particularly, it relates to a process for ammoxidation which utilizes a tellurium-free metal oxide catalyst.

BACKGROUND OF THE INVENTION

There are a number of known processes for ammoxidation reactions of organic compounds. The present invention relates to reactions using a metal oxide catalyst at a temperature of from 300° C. to 600° C. Examples of organic compounds include olefinic hydrocarbons, alcohols, aldehydes, alkyl substituted aromatic hydrocarbons, and alkyl substituted heterocyclic compounds having nitrogen, oxygen and sulfur, etc., as hetero atoms.

It has been described in U.S. Pat. Nos. 2,904,580, 3,152,170, 3,094,565, 3,094,552, 3,197,419, 3,308,151, 3,911,089, 4,139,552, 3,542,843, 3,591,620, etc., that metal oxide catalysts containing molybdenum and bismuth, etc., and metal oxide catalysts containing antimony and tin, iron or uranium are useful for ammoxidation of propylene, isobutene and methanol, etc. It has been described in U.S. Pat. Nos. 2,499,055, 2,838,558, 2,510,605, 3,959,297, etc., that metal oxide catalysts containing vanadium are useful for ammoxidation of alkyl substituted aromatic hydrocarbons or alkyl substituted heterocyclic compounds.

During the ammoxidation of these organic compounds, the activity of the catalyst often deteriorates after being used for a long period of time. The degree of deterioration varies with the kind of catalyst and the conditions under which the catalyst is used.

The activity deterioration has various causes. Accordingly, a number of different approaches have been investigated with respect to eliminating the deterioration.

However, the specific reason for the deterioration is not always obvious which makes it difficult to determine a method of eliminating the deterioration. Some examples of proposed methods require change of the reaction condition, partial replacement of the catalyst, exchange of all the catalysts, or regeneration of the deteriorated catalyst taken out of the reactor. Such methods have not been found to be economical.

It is very advantageous if activity of the catalyst is maintained or recovered without adding a fresh catalyst or interrupting the reaction.

As to this, U.S. Pat. No. 3,882,159 discloses a process for regenerating catalysts which comprises contacting in situ a molybdenum containing fluidized-bed catalyst which has become deteriorated by loss of molybdenum during an ammoxidation reaction of propylene with fluidized-bed particles composed of an essentially inert carrier and molybdenum oxide at the reaction temperature. This U.S. Patent is concerned with only regeneration of a molybdenum containing fluidized-bed catalyst, wherein molybdenum oxide supported on an inert carrier is simply used as the regenerating agent.

U.S. Pat. No. 3,236,782 discloses a process for regenerating metal oxide catalysts containing at least Cr, V, Mo or W which comprises contacting the catalyst with a vapor of a compound of the same metal as that present in the catalyst. The process disclosed in this U.S. Patent requires a complicated operation in that the catalyst component is introduced as a vapor into the reaction zone.

SUMMARY OF THE INVENTION

An object of the present invention is to prevent catalyst deterioration during ammoxidation using a tellurium-free metal oxide catalyst. This and other objects of the invention are attained by contacting said catalyst with a tellurium component or a tellurium-molybdenum component generated as a gaseous phase from a tellurium source or a tellurium-molybdenum source.

Accordingly, in the present invention, the ammoxidation process comprises carrying out ammoxidation of organic compounds at a temperature of from 300° C. to 600° C. using a tellurium-free metal oxide catalyst. The ammoxidation is carried out in the presence of (a) an elemental tellurium or a tellurium compound which is in contact with said catalyst or in the presence of (a) elemental tellurium or a tellurium compound and (b) a molybdenum compound which are in contact with said catalyst. In particularly preferred embodiments of the present invention, it is possible to use any of a dry physical mixture of said catalyst and a tellurium containing solid, a dry physical mixture of said catalyst, a tellurium containing solid and a molybdenum containing solid, or a dry physical mixture of said catalyst and a tellurium-molybdenum containing solid.

By utilizing the present invention, it is possible to improve the selectivity of the metal oxide catalyst for the desired product and improve the reaction rate. Furthermore, undesirable reduction of the reaction rate with the passage of time is improved upon and there is restoration of the selectivity of the deteriorated catalyst for the desired product.

The process of the present invention can be applied to both a fixed-bed and a fluidized-bed. However, the invention can be particularly easily applied when the catalyst is used for a fluidized-bed reaction. If (a) the elemental tellurium or the tellurium compound and (b) the molybdenum compound are solid and have suitable physical properties (as described hereinafter), they can be easily added during the reaction.

In the fluidized-bed reaction, a portion of the catalyst can be easily withdrawn or added while the reaction is being conducted. These operations can be carried out continuously or intermittently by a simple and conventional means while the reaction is industrially carried out. Accordingly, when using a tellurium containing solid, a molybdenum containing solid or a tellurium-molybdenum containing solid as a catalyst activity improving agent according to the present invention, it is possible to easily add the agent while the fluidized-bed reaction is being conducted. The present invention does not result in losses due to production interruptions, because the invention can be practiced during the reaction. This is different from many known processes for regenerating catalysts. Of course, improvement of the selectivity and/or the activity can also be carried out when the catalyst and the tellurium containing solid, the catalyst, the tellurium containing solid and the molybdenum containing solid, or the catalyst and the tellurium-molybdenum containing solid are physically mixed in a dry state before initiation of the reaction and the resulting dry mixture is used for the reaction.

The mechanism by which the effects of the present invention are exhibited is not clear. However, it is believed that when using a tellurium containing solid and a molybdenum containing solid or a tellurium-molybdenum containing solid, a tellurium component and a molybdenum component (which are volatile or are changed to be volatile under the reacting condition) are formed. The components poison active sites on the catalyst participating in formation of undesirable by-products such as carbon dioxide or carbon monoxide, etc., to control the formation of such by-products. Accordingly, selectivity for desired products is improved. The molybdenum component in a vapor phase migrates at the same time and deposits on the catalyst to restore the active sites or to produce fresh active sites. This is advantageous for the formation of the desired product in cooperation with the tellurium component. Therefore, the reaction rate is increased. When using a tellurium containing solid, molybdenum containing solid or a tellurium-molybdenum containing solid, the effect is exhibited in a comparatively short time. In many cases, the effect can be clearly seen within 1 to 2 hours. Furthermore, duration of the effect is excellent. Accordingly, transfer of the tellurium component and the molybdenum component from the tellurium-molybdenum containing solid is carried out at a comparatively high transfer rate. It is also believed that the tellurium component and molybdenum component deposited on the catalyst have high affinity with respect to the catalyst components. Accordingly, once attached to the catalyst, the tellurium component and the molybdenum component are not easily separated.

The mechanism suggested is based on speculation. The details of how the present invention operates are not sufficiently clear at this time. The present invention comprises contacting the tellurium-free metal oxide catalyst with (a) an elemental tellurium or a tellurium compound or (a) an elemental tellurium or a tellurium compound and (b) a molybdenum compound while the reaction is conducted. At present, the means for utilizing this invention and obtaining the desired objects should be understood in view of the above described mechanism.

DETAILED DESCRIPTION OF THE INVENTION

In the following, the present invention is illustrated in detail.

Metal Oxide Catalyst

The metal oxide catalyst used in the present invention includes various catalysts for ammoxidation which do not contain tellurium, as shown in the above described patent publications. The process of the present invention can be equally applied to these known tellurium-free metal oxide catalysts.

Useful metal oxide catalysts contain at least one element selected from the group consisting of antimony, molybdenum and vanadium.

More specifically, the catalyst used in the present invention is preferably selected from the following catalysts. These catalysts may be used by themselves or may be supported on various carriers such as silica, silica-alumina, alumina, silica-titania, titania or zirconia, etc.

(1) $Sb_{10}A_aB_bC_cO_x$ (composition by atomic ratio)

A = At least one element selected from the group consisting of Fe, Co, Ni, Mn, U, Ce, Sn, Cu and Ti.

B = At least one element selected from the group consisting of V, Mo and W.

C = At least one element selected from the group consisting of Mg, Ca, Sr, Ba, La, Ti, Zr, Nb, Ta, Cr, Re, Ru, Os, Rh, Ir, Pd, Pt, Ag, Zn, Cd, B, Al, Ga, In, Tl, Ge, Pb, P, As, Bi, S and Se.

a = 1-10
b = 0-5
c = 0-10 x is defined below.

(2) $Mo_{10}D_dE_eF_fO_x$ (composition by atomic ratio)

D = At least one element selected from the group consisting of Fe, Ni, Co, Mn, Cr, Mg, Ca, Cu, Zn, La, Ce, Al and Sn.

E = At least one element selected from the group consisting of Sb, Bi, As, P and B.

F = At least one element selected from the group consisting of K, Rb and Cs.

d = 0-10
e = 0.1-10
f = 0-3 x is defined below.

(3) $V_{10}G_gH_hO_x$ (composition by atomic ratio)

G = AT least one element selected from the group consisting of Li, Na, K, Rb, Cs, Tl, Mg, Ca, Sr and Ba.

H = At least one element selected from the group consisting of La, Ce, Ti, Zr, Nb, Ta, Cr, Mo, W, Mn, Re, Fe, Ru, Os, Co, Rh, Ir, Ni, Pd, Pt, Cu, Ag, Zn, Cd, B, Al, Ga, In, Ge, Sn, Pd, P, As, Sb, Bi, S and Se.

g = 0-5
h = 0-20 wherein O represents oxygen, and x represents the number of oxygen corresponding to oxides formed by combining elements in each component (which are common to the above (1) to (3)).

The catalyst may have any form. In case of the fixed-bed reaction, catalysts having various shapes such as pellets or balls having a size of several mm are used, preferably about 1 to 10 mm, more preferably 2 to 5 mm. In case of the fluidized-bed reaction, catalysts having a particle size ranging from 5 to 200 microns, preferably 10 to 150 microns are used.

Elemental Tellurium, Tellurium Compound and Molybdenum Compound (activity improving agent)

There are a number of useful substances which can make up (a) the elemental tellurium or tellurium compound and (b) the molybdenum compound used as the activity improving agent in the present invention. In preferred embodiments of the present invention, the catalyst to be processed for improving the activity thereof is a catalyst for a fluidized-bed reaction and the improvement of activity is carried out while conducting the fluidized-bed reaction. Accordingly, when the activity improving agent is solid, it is preferably comprised of particles capable of being fluidized under the reaction conditions such that the activity improving agent is sufficiently blended with the catalyst. When using a finely-divided activity improving agent, these finely-divided particles are preferably carefully introduced from a lower portion of the fluidized-bed reactor so that they are dispersed throughout the catalyst bed.

(1) Kind and Production

Examples of the tellurium containing solid used in the present invention include tellurium, tellurium monoxide, tellurium dioxide, tellurium trioxide, tellurous acid, telluric acid and organic tellurium compounds, those supported on an inert carrier such as silica, alumina, silica-alumina, titania, silica-titania or zirconia, etc., and tellurium containing metal oxide catalyst enriched with tellurium, preferably tellurium oxides, hydrated tellurium oxides, and tellurium containing metal oxide catalyst enriched with tellurium.

Tellurium metal, tellurium dioxide, tellurium trioxide, tellurous acid, telluric acid and organic tellurium compounds, etc., may be commercially available or can be prepared from various tellurium sources using known methods.

When using the tellurium component supported on various carriers, various means of support can be utilized. For example, tellurium metal, tellurium dioxide, tellurous acid, telluric acid, tellurium nitrate, basic tellurium nitrate, tellurium halide, tellurium sulfate and organic tellurium compounds, etc., can be used as a tellurium source. These compounds are mixed with a carrier material such as silica sol, alumina sol or titania sol, etc., followed by spray-drying. Alternatively, a carrier previously prepared can be impregnated with a solution prepared by dissolving the above described tellurium sources. Further, when using a tellurium enriched fluidized-bed catalyst for this purpose, known processes for producing catalysts can be suitably used. Moreover, a catalyst prepared using a known suitable process may be impregnated with a solution containing the tellurium component directly or after use for the reaction, followed by drying and calcining. During calcination, it is preferable to maintain a temperature of 900° C. or less for 0.5 to 50 hours.

Examples of molybdenum compounds include molybdenum dioxide, molybdenum trioxide, molybdic acid, ammonium paramolybdate, ammonium phosphomolybdate and phosphomolybdic acid, and those supported on an inert carrier as described above, and molybdenum enriched metal oxide catalysts, preferably molybdenum oxides, hydrated molybdenum oxides, ammonium paramolybdate, and molybdenum enriched metal oxide catalysts.

Preparations of the molybdenum containing solid can be carried out using the same processes used in preparing the above described tellurium containing solid.

The tellurium-molybdenum containing solid differs only because the tellurium component and the molybdenum component are present at the same time. It can be prepared by known suitable processes. For example, it can be prepared by blending the above described tellurium source and the molybdenum source and molding the resulting mixture, or by blending both of the above described sources with a carrier component and molding the resulting mixture. It is also possible to use a process for producing a fluidized-bed catalyst enriched with both tellurium and molybdenum.

The tellurium containing solid, the molybdenum containing solid and tellurium-molybdenum containing solid may contain, if desired, other elements in addition to tellurium and/or molybdenum. Namely, they may contain at least one element selected from the group consisting of alkali metals, alkaline earth metals, lanthanum, cerium, vanadium, niobium, chromium, tungsten, manganese, iron, cobalt, nickel, copper, zinc, cadmium, boron, aluminium, gallium, germanium, tin, lead, phosphorus, arsenic, antimony, bismuth, sulfur and selenium. If the solid has an activity and the reaction rate is equal to or slightly lower than that of the catalyst when the reaction is carried out using the solid alone, a positive effect is observed when the amount of addition is not excessive (for example, about 50% or more), even though the selectivity to the desired product is somewhat inferior. When using the tellurium enriched catalyst or the tellurium-molybdenum enriched catalyst for the purpose of the present invention, the mixing ratio is not strictly limited. if the reaction rate thereof and selectivity to the desired product are not greatly different from those of the catalyst used.

Various different effects are obtained with the activity improving agents when the above described various elements are used in addition to tellurium and/or molybdenum. The addition of these elements can be used for increasing or decreasing the transfer rate of the tellurium component and/or molybdenum component to the catalyst. Further, these elements can be used for controlling the physical properties of the activity improving agent.

The mixing ratio in the activity improving agent should be selected taking into consideration the above described factors.

(2) Tellurium Content and Molybdenum Content

Since it is believed, as described above, that the tellurium component and the molybdenum component exhibit the effect directly or after conversion into volatile compounds, the effect decreases, if the amounts of the tellurium component and the molybdenum component are too small. Particularly, when using tellurium and molybdenum supported on an inert carrier or using a catalyst enriched with these components, it may be necessary to add them in a large amount when the tellurium content and/or the molybdenum content thereof is too small.

However, since the tellurium and molybdenum compounds are not themselves the catalyst for the desired reaction, the catalyst may be diluted by their presence. Consequently, the volume of the reactor becomes insufficient for sufficiently carrying out the reaction.

In consideration of such circumstances, it is preferred that the tellurium content in the activity improving agents is 0.5% by weight or more, preferably 1% by weight or more, and the molybdenum content in the activity improving agents containing molybdenum is 0.1% by weight or more, preferably 0.5% by weight or more.

It is preferred that the ratio of molybdenum/ tellurium (atomic ratio) in the tellurium containing solid and the molybdenum containing solid or in the tellurium-molybdenum containing solid to be mixed with the catalyst is 0.05 to 10, preferably 0.05 to 5.

(3) Form

When using (a) an elemental tellurium or a tellurium compound, or (a) an elemental tellurium or a tellurium compound and (b) a molybdenum compound as they are, they may be introduced into the reactor as a powder or they may be physically blended with the catalyst in a dry condition and thereafter added to the reaction system.

When using the tellurium component and the molybdenum component as a solid, their physical properties are important. Its strength is important when used in a fixed-bed reaction. Namely, powdering and simultaneous volatilization of the tellurium component or the molybdenum component should be prevented because it increases the pressure drop of the reaction gas in the catalyst bed. When a fluidized-bed reaction is used, the activity improving agent is preferably fluidized so that it can be blended well with the catalyst. Further, in order for the tellurium component and the molybdenum component to be effectively used, the activity improving agent should be present in the reactor for the time necessary to be sufficiently mixed with the catalyst.

Accordingly, when a fluidized-bed reaction is being carried out, the activity improving agent preferably has a particle size comparatively similar to that of the catalyst and the value of (bulk density of the activity improving agent)/(bulk density of the catalyst) is in a range from 0.05 to 8, preferably a range from 0.2 to 0.6. Further, it is preferred for the fluidized-bed catalyst, in carrying out the present invention, to have a bulk density of 0.1 to 3 (g/ml) and a particle size of 5 to 200 microns.

Activity Improvement Processing

In the ammoxidation reaction according to the present invention, the activity improvement processing of the metal oxide catalyst is carried out at the same time by contacting the metal oxide catalyst with (a) an elemental tellurium or a tellurium compound or with (a) an elemental tellurium or a tellurium compound and (b) a molybdenum compound. Both the catalyst to be processed and the activity improving agent are preferably in a fluidized state.

The process of the present invention can also be applied to a fixed-bed reaction by physically blending the catalyst to be processed with the activity improving agent in a dry condition. However, the effect of improving the activty is particularly high when carrying out the processing while conducting the reaction in a fluidized state using a fluidized-bed catalyst. It is believed that, since movement of the activity improving agent is quick as is the movement of the catalyst, transfer of the tellurium component or the tellurium component and the molybdenum component to the catalyst is uniformly carried out to result in a good effect.

When the activity improving agent is solid, the total amount of the tellurium containing solid and the molybdenum containing solid or the amount of the tellurium-molybdenum containing solid is preferably 0.01% by weight or more based on the tellurium containing metal oxide catalyst. If the amount thereof is lower than 0.01% by weight, the effect is very poor and the duration of the effect deteriorates. With respect to the upper limit, there are various cases, which are similar to the cases described in the above described section "Kind and Production" for the activity improving agent.

The effect of the activity improving agent is exhibited by transfer of the tellurium component and the molybdenum component to the catalyst. Accordingly, from this standpoint, the apparent increment of tellurium content in the catalyst resulting from physically blending the catalyst with the activity improving agent in dry condition is preferably 0.001 to 15% by weight, more preferably 0.01 to 10% by weight, and the apparent increment of molybdenum therein is preferably 0.002 to 10% by weight, more preferably 0.01 to 5% by weight.

The apparent increment of tellurium content and the apparent increment of molybdenum content are defined as follows.

Apparent increment of tellurium content (%)=

$$\frac{\text{Weight of tellurium in activity improving agent added (g)}}{\text{Total weight of catalyst packed (g)}} \times 100$$

Apparent increment of molybdenum content (%)=

$$\frac{\text{Weight of molybdenum in activity improving agent added (g)}}{\text{Total weight of catalyst packed (g)}} \times 100$$

The amount of the activity improving agent which is preferably added depends upon properties of the activity improving agent. When the tellurium component and the molybdenum component have a high transfer rate, the activity improving agent is sufficient if used in an amount calculated from the desired tellurium and molybdenum contents.

The activity improving agent may be physically blended with the catalyst in a dry condition prior to initiation of the reaction or it may be added during the reaction, alone or as a mixture prepared by physically blending the agent with the catalyst in a dry condition. There are no problems with the fluidized-bed reaction, because the catalyst can be safely withdrawn and added while conducting the reaction.

Addition of the active improving agent can be carried out several times while observing the conditions of the reaction.

Although it is not necessary to contact the catalyst with the tellurium component together with the molybdenum component at the same time, the catalyst may be first contacted with the tellurium component and thereafter contacted with the molybdenum component, or the reverse operation may be carried out. However, it is preferable, if possible, to avoid the first addition of only the molybdenum component, because the selectivity for the desired product temporarily decreases by addition of only the molybdenum component at the beginning.

When only the elemental tellurium or the tellurium compound is physically blended with the catalyst in a dry condition, improvement of the selectivity for the desired product is very effectively carried out, but the reaction rate hardly varies or sometimes slightly decreases.

On the other hand, when only the molybdenum compound is physically blended with the catalyst in a dry condition, the selectivity for by-products is often increased and, consequently, the selectivity for the desired product decreases.

As described above, though the addition of the activity improving agent may be carried out using various techniques, it is necessary to add the tellurium component alone or to add both the tellurium component and the molybdenum component. The latter case is particularly preferable.

Condition for Ammoxidation

The conditions for carrying out the ammoxidation in accordance with the present invention are the same as those used for conventional ammoxidation of organic compounds such as propylene, isobutene, methanol, tert-butanol, methyl tert-butyl ether, toluene, xylene, picoline, etc.

Namely, the molar ratio of the feed gas is in a range of 1/0.3–10/0.5–5 as organic compound/oxygen/ammonia (molar ratio), and the reaction temperature is in a range of 300°–600° C. The reaction pressure used is in a range of atmospheric pressure to 3 kg/cm$^2$G or so. The feed gas used may be diluted with nitrogen, steam, carbon dioxide, carbon monoxide or helium, etc.

The effects of the present invention are illustrated below by reference to examples.

The yield of the desired product and the selectivity for the desired product are defined herein as follows.

$$\text{Yield (\%)} = \frac{\text{Weight of carbon in formed desired product}}{\text{Weight of carbon in organic compound fed as starting material}} \times 100$$

$$\text{Selectivity (\%)} = \frac{\text{Weight of carbon in formed desired product}}{\text{Weight of carbon in organic compound reacted}} \times 100$$

The condition for the activity test is as follows.
(1) Ammoxidation of Propylene A fluidized-bed reactor having an inner diameter of 5 cm (2 inches) and a height of 2 m was packed with a catalyst in an amount suitably selected from the range of 1,200 g to 1,800 g. Into this reactor, a gas having the following composition was introduced to result in an apparent linear velocity of 15 cm/sec. The reaction pressure was atmospheric pressure.

$O_2$ (introduced as air)/propylene = 2.10 (molar ratio)
$NH_3$/propylene = 1.15 (molar ratio)

The contact time is defined as follows.

$$\text{Contact time} = \frac{\text{Volume of catalyst packed (l)*}}{\text{Flow rate of feed gas (l/sec)}} \text{ (sec)}$$

*On the basis of apparent bulk density of the catalyst (2) Ammoxidation of Toluene The same reactor as that used for the above described ammoxidation of propylene was used and the gas was introduced so as to result in an apparent linear velocity of 15 cm/sec. The reaction pressure was atmospheric.

| | |
|---|---|
| $O_2$ (supplied as air)/toluene = | 2.5 (molar ratio) |
| $NH_3$/toluene = | 1.5 (molar ratio) |
| $H_2O$/toluene = | 2.5 (molar ratio) |

The definition of the contact time is the same as described above.

EXAMPLE 1

An activity test was carried out under testing condition (1) using a fluidized-bed catalyst having the empirical formula: $Fe_{10}Sb_{25}V_{0.1}P_{0.5}O_{65.4}(SiO_2)_{30}$.

The yield of acrylonitrile was 74.2%.

When a tellurium containing solid containing 32% by weight of Te (the balance consisted of oxygen and silicon) (the balance in the following examples means the same, unless otherwise stated) was blended so as to result in an amount of 3.5% by weight based on the catalyst to carry out the reaction, the yield of acrylonitrile after 2 hours became 77.2%. When the reaction was carried out for another 2 hours, the yield did not vary.

EXAMPLE 2

An activity test was carried out under testing condition (1) using a fluidized-bed catalyst having the empirical formula: $W_{0.5}Co_5Fe_{10}Sb_{25}O_{71.5}(SiO_2)_{30}$.

The yield of acrylonitrile was 74.1% at the beginning, but the activity of the catalyst deteriorated, because it was used for a long time, resulting in a yield of 65.2%.

When a tellurium containing solid containing 32% by weight of Te was blended therewith so as to result in an amount of 1.5% by weight based on the catalyst to carry out the reaction, the yield of acrylonitrile after 3 hours became 72.8%.

EXAMPLE 3

An activity test was carried out under testing condition (1) using a fluidized-bed catalyst having the empirical formula: $Sn_{10}Sb_{25}O_{70}(SiO_2)_{30}$.

The yield of acrylonitrile was 68.9%.

When a tellurium containing solid containing 16% by weight of Te was blended therewith so as to result in an amount of 3.5% by weight based on the catalyst to carry out the reaction, the yield of acrylonitrile after 2 hours became 73.5%.

EXAMPLE 4

An activity test was carried out under testing condition (1) using a fluidized-bed catalyst having the empirical formula: $U_{10}Sb_{30}O_{86.7}(SiO_2)_{60}$.

The yield of acrylonitrile was 69.5% at the beginning, but the activity of the catalyst deteriorated, because it was used for a long time, resulting in a yield of 64.8%.

When a tellurium containing solid containing 32% by weight of Te was blended therewith so as to result in an amount of 1.5% by weight based on the catalyst to carry out the reaction, the yield of acrylonitrile after 2 hours became 70.2%.

EXAMPLE 5

An activity test was carried out under testing condition (1) using a fluidized-bed catalyst having the empirical formula: $P_{0.5}K_{0.1}Fe_3Ni_{2.5}Co_{4.5}Bi_1Mo_{12}O_{50.3}(SiO_2)_{45}$.

The yield of acrylonitrile was 75.3% at the beginning, but the activity of the catalyst deteriorated, because it was used for a long time, resulting in a yield of 71.8%.

When a tellurium containing solid containing 16% by weight of Te was blended therewith so as to result in an amount of 0.5% by weight based on the catalyst to carry out the reaction, the yield of acrylonitrile became 73.8% after 1.5 hours and 74.2% after 5 hours.

EXAMPLE 6

An activity test was carried out under testing condition (2) using a fluidized-bed catalyst having the empirical formula: $P_1V_{12}O_{32.5}(SiO_2)_{50}$.

The yield of benzonitrile was 75.2%.

When a tellurium containing solid containing 16% by weight of Te was blended therewith so as to result in an amount of 0.5% by weight based on the catalyst to carry out the reaction, the yield of benzonitrile after 2 hours became 76.3%.

The results and conditions of Examples 1 to 6 are summarized in the following Table 1.

TABLE 1

| Example | Composition of Catalyst (atomic ratio) | Condition of Activity Test | Reaction Temperature (°C.) | Contact Time (sec) | Yield of Product (%) | Carbon Dioxide Gas (%) | Conversion of Hydrocarbon (%) |
|---|---|---|---|---|---|---|---|
| 1 | $Fe_{10}Sb_{25}V_{0.1}P_{0.5}O_{65.4}(SiO_2)_{30}$ | | | | | | |
| | Before blending | (1) | 460 | 7 | 74.2 | 11.3 | 97.2 |
| | Blending with Te containing solid | (1) | 460 | 7 | 77.2 | 9.7 | 96.0 |
| 2 | $W_{0.5}Co_5Fe_{10}Sb_{25}O_{71.5}(SiO_2)_{30}$ | | | | | | |
| | Before deterioration | (1) | 460 | 6 | 74.1 | 9.2 | 96.2 |
| | After deterioration | (1) | 460 | 6 | 65.2 | 12.3 | 92.4 |
| | Blending with Te containing solid | (1) | 460 | 6 | 72.8 | 9.5 | 93.1 |
| 3 | $Sn_{10}Sb_{25}O_{70}(SiO_2)_{70}$ | | | | | | |
| | Before blending | (1) | 460 | 7 | 68.9 | 11.3 | 92.0 |
| | Blending with Te containing solid | (1) | 460 | 7 | 73.5 | 9.5 | 92.5 |
| 4 | $U_{10}Sb_{30}O_{86.7}(SiO_2)_{60}$ | | | | | | |
| | Before deterioration | (1) | 470 | 7 | 69.5 | 9.8 | 95.1 |
| | After deterioration | (1) | 480 | 7 | 64.8 | 10.4 | 94.4 |
| | Blending with Te containing solid | (1) | 480 | 7 | 70.2 | 9.6 | 94.2 |
| 5 | $P_{0.5}K_{0.1}Fe_3Ni_{2.5}Co_{4.5}Bi_1Mo_{12}O_{52.2}(SiO_2)_{45}$ | | | | | | |
| | Before deterioration | (1) | 430 | 4 | 75.3 | 6.7 | 95.3 |
| | After deterioration | (1) | 440 | 4 | 71.8 | 7.2 | 95.3 |
| | Blending with Te containing solid | (1) | 440 | 4 | 74.2 | 6.5 | 94.5 |
| 6 | $P_1V_{12}O_{32.5}(SiO_2)_{50}$ | | | | | | |
| | Before blending | (2) | 450 | 4.5 | 75.2 | 14.9 | 98.9 |
| | Blending with Te containing solid | (2) | 450 | 4.5 | 76.3 | 13.1 | 96.3 |

EXAMPLE 7

An activity test was carried out under testing condition (1) using a fluidized-bed catalyst having the empirical formula: $Fe_{10}Sb_{25}V_{0.1}P_{0.05}O_{65.4}(SiO_2)_{30}$.

The yield of acrylonitrile was 74.2%.

When a tellurium-molybdenum containing solid containing 38.3% by weight of tellurium, 2.9% by weight of molybdenum and 47.8% by weight of silicon dioxide was blended therewith so as to result in an amount of 1.0% by weight based on the catalyst and the reaction was continued for 2 hours, the yield of acrylonitrile became 78.1%. Thereafter, the reaction was continued for 3 hours, but the yield of acrylonitrile did not vary.

EXAMPLE 8

An activity test was carried out under testing condition (1) using a fluidized-bed catalyst having the empirical formula: $W_{0.5}Co_5Fe_{10}Sb_{25}O_{71.5}(SiO_2)_{30}$.

The yield of acrylonitrile was 74.1% at the beginning, but it became 70.2% when used for a long time.

A telluriumm-molybdenum containing solid containing 35.2% by weight of tellurium, 7.9% by weight of molybdenum and 44.0% by weight of silicon dioxide was added thereto in an amount of 1.1% by weight based on the catalyst while conducting the reaction. After blending the tellurium-molybdenum containing solid, with the catalyst, the yield of acrylonitrile became 73.9% after 2 hours.

On the other hand, the above described tellurium-molybdenum containing solid was added to a fresh catalyst in an amount of 1.1% by weight based on the catalyst, and an activity test was carried out similarly under testing condition (1). After 2 hours, the yield of acrylonitrile became 76.3%.

EXAMPLE 9

An activity test was carried out under testing condition (1) using a fluidized-bed catalyst having the empirical formula: $Sn_{10}Sb_{25}O_{70}(SiO_2)_{30}$.

The yield of acrylonitrile was 68.9%.

When the reaction was carried out by blending with a tellurium containing solid containing 20.0% by weight of tellurium (composed of silicon and oxygen in addition to tellurium) in an amount of 1.5% by weight based on the catalyst and a molybdenum containing solid containing 66.7% of molybdenum (composed of silicon and oxygen in addition to molybdenum) in an amount of 0.15% by weight based on the catalyst, the yield of acrylonitrile became 74.3% after 2 hours.

EXAMPLE 10

An activity test was carried out under the conditions of activity test (1) using a fluidized-bed catalyst having the empirical formula: $U_{10}Sb_{30}O_{86.7}(SiO_2)_{60}$.

The yield of acrylonitrile was 69.5% at the beginning, but the activity of the catalyst deteriorated, because it was used for a long time, resulting in a yield of 66.8%.

When the same tellurium-molybdenum containing solid as that used in Example 8 was blended therewith so as to result in an amount of 0.85% by weight based on the catalyst, the yield of acrylonitrile became 72.2% after 2 hours.

EXAMPLE 11

An activity test was carried out under testing condition (1) using a fluidized-bed catalyst having the empirical formula: $P_{0.5}K_{0.1}Fe_3Ni_{2.5}Co_{4.5}Bi_1Mo_{12}O_{50.3}(SiO_2)_{45}$.

The yield of acrylonitrile was 75.3% at the beginning, but the activity of the catalyst deteriorated, because it was used for a long time, resulting in a yield of 72.0%.

When the same tellurium-molybdenum containing solid as that used in Example 8 was blended therewith so as to result in an amount of 0.3% by weight based on the catalyst to carry out the reaction, the yield of acrylonitrile became 76.3% after 3 hours.

EXAMPLE 12

An activity test was carried out under testing condition (2) using a fluidized-bed catalyst having the empirical formula: $P_1V_{12}O_{32.5}(SiO_2)_{50}$.

The yield of benzonitrile was 75.2%.

When the same tellurium-molybdenum containing solid as that used in Example 7 was blended therewith so as to result in an amount of 0.26% by weight based on the catalyst to carry out the reaction, the yield of benzonitrile became 77.5% after 2 hours.

The results and conditions of Examples 7 to 12 are summarized in the following Table 2.

TABLE 2

| Example | Composition of Catalyst (atomic ratio) | Condition of Activity Test | Reaction Temperature (°C.) | Contact Time (sec) | Yield of Desired Product (%) | Total Conversion of Organic Compound (%) |
|---|---|---|---|---|---|---|
| 7 | $F_{10}Sb_{25}V_{0.1}P_{0.5}O_{65.4}(SiO_2)_{30}$ | | | | | |
| | Before processing | (1) | 460 | 7 | Acrylonitrile 74.2 | Propylene 97.2 |
| | After activity improvement processing | " | " | " | 78.1 | 98.0 |
| 8 | $W_{0.5}Co_5Fe_{10}Sb_{25}O_{71.5}(SiO_2)_{30}$ | | | | | |
| | Before deterioration | (1) | 460 | 6 | Acrylonitrile 74.1 | Propylene 96.2 |
| | After deterioration | " | " | " | 70.2 | 93.2 |
| | After activity improvement processing (i) | " | " | " | 73.9 | 96.5 |
| | After activity improvement processing (ii) | " | " | " | 76.3 | 98.1 |
| 9 | $Sn_{10}Sb_{25}O_{70}(SiO_2)_{30}$ | | | | | |
| | Before processing | (1) | 460 | 7 | Acrylonitrile 68.9 | Propylene 92.0 |
| | After activity improvement processing | " | " | " | 74.3 | 95.2 |
| 10 | $U_{10}Sb_{30}O_{86.7}(SiO_2)_{60}$ | | | | | |
| | Before deterioration | (1) | 470 | 7 | Acrylonitrile 69.5 | Propylene 95.1 |
| | After deterioration | " | 480 | " | 66.8 | 93.8 |
| | After activity improvement processing | " | " | " | 72.2 | 97.5 |
| 11 | $P_{0.5}K_{0.1}Fe_3Ni_{2.5}Co_{4.5}Bi_1Mo_{12}O_{50.3}(SiO_2)_{45}$ | | | | | |
| | Before deterioration | (1) | 430 | 4 | Acrylonitrile 75.3 | Propylene 95.3 |
| | After deterioration | " | 440 | " | 72.0 | 95.2 |
| | After activity improvement processing | " | " | " | 76.3 | 97.2 |
| 12 | $P_1V_{12}O_{32.5}(SiO_2)_{50}$ | | | | | |
| | Before processing | (2) | 450 | 4.5 | Benzonitrile 75.2 | Toluene 98.9 |
| | After activity improvement processing | " | " | " | 77.5 | 99.2 |

From the results obtained as shown in Tables 1 and 2, it can be seen that when blending the tellurium containing solid, the tellurium containing solid and molybdenum containing solid or the tellurium-molybdenum containing solid as a catalyst activity improving agent with a fresh catalysts or the spent catalyst having a deteriorated activity to carry out the reaction, the reaction results are further improved as compared with that of the fresh catalyst alone or they become equal to or higher than that of the catalyst before the deterioration. Thus, the treatment of blending the activity improving agents described above provides an unexpected result in providing the advantages that the deteriorated catalyst is recovered and the activity of the fresh catalyst is further improved without adding a fresh catalyst or interrupting the reaction.

While the invention has been described in detail and with reference to specific embodiments thereof, it will be apparent to one skilled in the art that various changes and modifications can be made therein without departing from the spirit and scope thereof.

What is claimed is:

1. In a process for producing a nitrile by ammoxidation of an organic compound selected from the group consisting of propylene, isobutene, methanol, tert-butanol, methyl tert-butyl ether, toluene and xylene using a packed metal oxide catalyst containing at least one element selected from the group consisting of antimony, molybdenum and vanadium at a temperature of 300° C. to 600° C., at atmospheric pressure to 3 kg/cm²G and at a molar ratio of feed gas in the range of 1/0.3–10/0.5–5 as organic compound/oxygen/ammonia (molar ratio), the improvement which comprises carrying out the ammoxidation in the presence of an activity improving agent which is selected from the group consisting of (a) elemental tellurium which is in contact with said catalyst in the course of the ammoxidation; (b) a tellurium compound which is in contact with said catalyst in the course of the ammoxidation; (c) elemental tellurium and a molybdenum compound which are in contact with said catalyst in the course of the ammoxidation; or (d) a tellurium compound and a molybdenum compound which are in contact with said catalyst in the course of the ammoxidation, all of which are volatile or are changed to be volatile under the ammoxidation conditions, said activity promoting agent (a) to (d) being present in a catalytically effective amount, the activity improving agent being physically blended with the metal oxide catalyst prior to use in the ammoxidation in the form of a solid, wherein the amount of activity improving agent in the form of a solid is 0.01% by weight or more based on the metal oxide catalyst, wherein the apparent increment of tellurium content in the packed catalyst which is prepared by physically blending the metal oxide catalyst with the activity improving agent in the dry condition is 0.001 to 15% by weight, and the apparent increment of molybdenum content in the packed catalyst is 0.002 to 10% by weight, wherein the apparent increment of the tellurium content and the apparent increment of the molybdenum content are defined as follows:

Apparent increment of tellurium content (%)=

$$\frac{\text{Weight of tellurium in activity improving agent added (g)}}{\text{Total weight of packed catalyst (g)}} \times 100$$

$$\frac{\text{Weight at molybdenum in activity improving agent added (g)}}{\text{Total weight of packed catalyst (g)}} \times 100$$

and wherein said metal oxide catalyst is selected from the following catalysts:

1. $Sb_{10}A_aB_bC_cO_x$ (composition by atomic ratio)
   A = At least one element selected from the group consisting of Fe, Co, Ni, Mn, U, Ce, Sn, Cu and Ti;
   B = At least one element selected from the group consisting of V, Mo, and W;
   C = At least one element selected from the group consisting of Mg, Zn, boron, Al, Pb, P, and Bi;
   a = 1–10;
   b = 0–5;
   c = 0–10;
   x is defined below;

2. $Mo_{10}D_dE_eF_fO_x$ (composition by atomic ratio)
   D = At least one element selected from the group consisting of Fe, Ni, Co, Mn, Cr, Mg, Zn, Ce, and Sn;
   E = At least one element selected from the group consisting of Sb, Bi, P and B;
   F = At least one element selected from the group consisting of K, Rb and Cs;
   d = 0–10;
   e = 0.1–10;
   f = 0–3;
   x is defined below; and 3. $V_{10}G_gH_hO_x$ (composition by atomic ratio)
   G = At least one element selected from the group consisting of Li, Na, K, Rb, Cs, Mg, Ca, Sr and Ba;
   H = At least one element selected from the group consisting of Ti, Mo, W, Mn, Fe, Co, Ni, Zn, B, Sn, P, Sb, and Bi;
   g = 0–5;
   h = 0.20;

wherein O represents oxygen, and x represents the number of oxygen atoms corresponding to oxides formed by combining elements in each component which are common to the above catalysts (1) to (3).

* * * * *